United States Patent [19]

Gosteli

[11] 4,430,510

[45] Feb. 7, 1984

[54] PROCESS FOR THE PREPARATION OF 2-(2,4-DICHLOROPHENOXY)-PHENYLACETIC ACID

[75] Inventor: Jacques Gosteli, Basel, Switzerland

[73] Assignee: Schering Corporation, Kenilworth, N.J.

[21] Appl. No.: 381,250

[22] Filed: May 24, 1982

[30] Foreign Application Priority Data

Jun. 18, 1981 [CH] Switzerland .......................... 4016/81

[51] Int. Cl.$^3$ ....................... C07C 59/00; C07C 65/00
[52] U.S. Cl. .................................................. 562/465
[58] Field of Search ........................................ 562/465

[56] References Cited

U.S. PATENT DOCUMENTS 3,766,263 10/1972 Godfrey ............................... 562/465

FOREIGN PATENT DOCUMENTS 2720427 11/1977 Fed. Rep. of Germany ........ 500/21

Primary Examiner—Paul J. Killos
Attorney, Agent, or Firm—Stephen I. Miller; Gerald S. Rosen; Bruce M. Eisen

[57] ABSTRACT

The present invention relates to a novel process for the preparation of 2-(2,4-dichlorophenoxy)-phenylacetic acid a compound having useful anti-inflammatory properties. The process comprises reacting a 2-halo-phenylacetic acid or a salt thereof under basic conditions in the presence of metallic copper with 2,4-dichlorophenol or a salt thereof.

20 Claims, No Drawings

PROCESS FOR THE PREPARATION OF 2-(2,4-DICHLOROPHENOXY)-PHENYLACETIC ACID

This invention relates to a process for the preparation of 2-(2,4-dichlorophenoxy)-phenylacetic acid a compound having useful anti-inflammatory activity.

A process for the preparation of 2-(2,4-dichlorophenoxy)-phenyl-acetic acid is described in DOS No. 2,117,826 and the corresponding British patent specification 1,308,327. In this process 2-chloroacetophenone is reacted with 2,4-dichlorophenol (or the corresponding phenolate) and thereafter the resulting 2-(2,4-dichlorophenoxy)-acetophenone is subjected to the Willgerodt reaction. The resulting thioacetmorpholide is then saponified with alkali to give 2-(2,4-dichlorophenoxy)-phenylacetic acid. The aforementioned multistep process has the distadvantage of poor availability of 2-chloroacetophenone and only moderate yield (up to 37%) and is therefore economically unattractive.

We have now found that 2-(2,4-dichlorophenoxy)-phenylacetic acid may be prepared in a single step and in good yield by directly reacting a 2-halophenylacetic acid starting material with a 2,4-dichlorophenol starting material under specified conditions.

Accordingly, the present invention provides a process for the preparation of 2-(2,4-dichlorophenoxy)-phenylacetic and its salts characterised in that a 2-halophenylacetic acid or a salt thereof is reacted under basic conditions in the presence of metallic copper, preferably in a non-polar medium, with 2,4-dichlorophenol or a salt thereof.

Since the halogen atom of the 2-halophenylacetic starting material is not activated, it is surprising that the process in accordance with the invention proceeds at all. We have found that not only does the process proceed, but that it also gives yields significantly higher than the aforementioned prior art process. The relatively high yields obtainable in the process in accordance with the invention, together with the ready availability of the 2-halophenylacetic acid starting materials, render the process economically attractive. Further, since the catalyst employed in the present process is solid it is readily removed at the end of the reaction by simple filtration or like techniques. Thus, difficulties associated with the removal of soluble metal catalysts are avoided. This is of importance where environmental factors necessitate recovery of the metal catalyst before disposal of waste reaction products.

The process of the invention is effected under basic conditions. The basic conditions may be achieved by employing the 2-halophenylacetic acid and 2,4-dichlorophenol starting materials in free form and reacting them in the presence of a suitable base or, alternatively, by first forming a salt of the starting materials with the suitable base and then employing this basic salt as reactant. Suitable bases are those capable of forming phenolates with the 2,4-dichlorophenol starting material. Included are alkali metal and alkaline earth metal bases such as the hydroxides, bicarbonates and, in particular, the carbonates. Preferred bases are sodium and potassium hydroxide and bicarbonate and, in particular, sodium carbonate and especially potassium carbonate. The corresponding hydroxides, bicarbonates and carbonates of calcium and magnesium may be used in analogous manner.

The 2,4-dichlorophenol starting material is preferably present in an excess over that required by stoichiometry so as to react as much as possible of the 2-halophenylacetic acid, the mole ratio of 2,4-dichlorophenol starting material to 2-halophenylacetic acid starting material being preferably about 2:1. The ratio of the number of equivalents of base metal cation present in the reaction mixture to the number of moles of 2-halophenylacetic acid starting material is preferably also about 4 to 1 that is the base is present in about double the amount of the 2,4-dichlorophenol starting material. The 2-halophenylacetic acid starting material may suitably be 2-bromophenylacetic acid or, preferably, 2-chlorophenylacetic acid.

The metallic copper catalyst is preferably in the form of finely divided metallic copper, this active form being preparable according to the method of R. Q. Brewster and T. Groening, Org. Synth. Coll. Vol. II 446; John Wiley and Sons Inc. New York, 1943. Conveniently the mole ratio of catalyst to 2-halophenylacetic acid is about 0.3:1.

The process of the invention may be carried out in a polar medium such as a tertiary amide, for instance dimethylformamide or N-methyl-pyrrolidone, or more preferably in a non-polar medium such as an aromatic hydrocarbon, for instance tetralin or most preferably toluene. Other suitable non-polar media include aliphatic and cycloaliphatic hydrocarbons such as light petroleum or ligroin having a boiling range between 100° and 200° C. To reduce any phenol auto-oxidation side reactions, the reaction may, if desired, be effected under an inert atmosphere.

The reaction time will be dependent upon the choice of conditions usually ranging from about 1 hour to over 12 hours. When the reaction is effectively complete, isolation of the product may be effected in conventional manner.

The invention will now be illustrated by way of the following examples:

EXAMPLE 1

A mixture of 8.5 g 2-chlorophenylacetic acid, 16.2 g 2,4-dichlorophenol (95% pure), 13.8 g powdered potassium carbonate (potash), 1 g active copper prepared by the aforementioned method of Brewster and Groenig and 50 ml 1,2,3,4-tetrahydronaphthalene (tetralin) is stirred under a nitrogen atmosphere. With the aid of an oilbath, the temperature of the mixture is raised over a period of one hour to 145°–150° C. During the reaction carbon dioxide and water are evolved. The mixture is stirred for an hour at this temperature, allowed to cool, the suspension diluted with toluene and then poured into 250 ml 5% sodium bicarbonate solution. After extraction and separation of the layers, the organic layer is extracted with two 100 ml portions of bicarbonate solution, the aqueous extracts combined and then filtered through Celite (filter aid). The aqueous filtrate is washed with toluene and then under stirring acidified with 70 ml 6 N hydrochloric acid. The precipitated brown oil is dissolved in ether (2×250 ml), and the ethereal solution washed twice with water and once with brine, dried over sodium sulfate and treated with active carbon. After filtration and concentration in a rotary evaporator, a crystalline crude product is obtained which is recrystallized from ether-hexane. The yield is 7.8 g of crystals with m.p. 130°–133° C. A second crop (0.8 g) of the product having the same melting point is obtained by concentration of the mother liquors. Total yield=8.6 g (57.9% of theory).

EXAMPLE 2

A mixture of 17.8 g 2-chlorophenylacetic acid, 33.9 g 2,4-dichlorophenol (95% pure), 28.9 g powdered potassium carbonate (potash), 2.1 g active copper (moist weight 7.3 g) is dissolved or suspended in 330 ml toluene in a 1 liter flask equipped with a stirrer and water-separator. The reaction mixture is gradually heated under stirring to reflux and refluxed for 12 hours. Towards the end of the reaction time, the reaction mass solidifies to a gray-green paste. After cooling, 500 ml 5% sodium bicarbonate solution are added and the mixture is stirred for 5 minutes. The phases are separated, the dark toluene layer is further extracted with 3 portions of 75 ml bicarbonate solution and the combined basic extract is washed with 250 ml toluene. The bicarbonate solution is now treated with active carbon, filtered and carefully acidified with 6 N hydrochloric acid (pH 1). The precipitated product is taken up in ether, the solution is washed twice with 100 ml portions of salt solution, dried over sodium sulfate and concentrated in a rotary evaporator. The residue is recrystallized from hexane. 18.4 g colourless crystals m.p. 135°–136° C. are obtained. A second, smaller crop (3.3 g) of product with melting point 128°–130° is obtained from the mother liquors. Total yield=21.7 g (69.3% of theory).

I claim:

1. A process for the preparation of salts of 2-(2,4-dichlorophenoxy)-phenylacetic acid, comprising reacting a 2-halophenylacetic acid or a salt thereof under basic conditions in the presence of metallic copper with 2,4-dichlorophenol or a salt thereof.

2. A process according to claim 1, wherein the reaction is carried out in a non-polar medium.

3. A process according to claim 1, wherein the process is carried out in an aromatic hydrocarbon.

4. A process according to claim 1, wherein the reaction is carried out in the presence of finely divided metallic copper.

5. A process according to claim 1, wherein the reaction is carried out in a non-polar medium in the presence of finely divided metallic copper.

6. A process according to claim 1, wherein the reaction is carried out in an aromatic hydrocarbon in the presence of finely divided metallic copper.

7. A process according to claim 1, wherein the reaction is carried out in the presence of toluene.

8. A process according to claim 1, wherein the reaction is carried out within a temperature range of 100° to 200° C.

9. A process according to claim 1, wherein the reaction is carried out at the reflux temperature of the reaction mixture.

10. A process according to claim 1, wherein the reaction is carried out within a temperature range of 100° to 200° C. in a non-polar medium.

11. A process according to claim 1, wherein the reaction is carried out within a temperature range of 100° to 200° C. in an aromatic hydrocarbon.

12. A process according to claim 1, wherein the reaction is carried out within a temperature range of 100° to 200° C. in a non-polar solvent in the presence of finely divided metallic copper.

13. A process according to claim 1, wherein the reaction is carried out within a temperature range of 100° to 200° C. in an aromatic hydrocarbon in the presence of finely divided metallic copper.

14. A process according to any one of claims 1 to 13, wherein the reaction is carried out in the presence of an alkali or alkaline-earth metal base.

15. A process according to any one of claims 1 to 13, wherein the reaction is carried out in the presence of an alkali or alkaline-earth metal carbonate.

16. A process according to claim 1, wherein the reaction is carried out in the presence of potassium carbonate.

17. A process according to claim 1, wherein the process is carried out in toluene at the reflux temperature of the reaction mixture and in the presence of potassium carbonate and finely divided metallic copper.

18. A process according to claim 1, wherein the salt of 2-(2,4-dichlorophenoxy)-phenylacetic acid salt is further reacted with a strong acid to form the corresponding 2-(2,4-dichlorophenoxy)-phenylacetic acid.

19. A process according to claim 18, wherein the strong acid is a mineral acid.

20. A process according to claim 18, wherein the strong acid is hydrochloric acid.

* * * * *